United States Patent
Sager et al.

(10) Patent No.: US 10,357,596 B2
(45) Date of Patent: Jul. 23, 2019

(54) BIOCORRODIBLE IMPLANTS HAVING A FUNCTIONALIZED COATING

(75) Inventors: Laura Sager, Zurich (CH); Nina Adden, Nuremberg (DE)

(73) Assignee: BIOTRONIK AG, Buelach (CH)

( * ) Notice: Subject to any disclaimer, the term of this patent is extended or adjusted under 35 U.S.C. 154(b) by 25 days.

(21) Appl. No.: 12/972,703

(22) Filed: Dec. 20, 2010

(65) Prior Publication Data
US 2011/0153006 A1 Jun. 23, 2011

Related U.S. Application Data

(60) Provisional application No. 61/288,348, filed on Dec. 21, 2009.

(51) Int. Cl.
| | | |
|---|---|---|
| *A61F 2/06* | (2013.01) | |
| *A61L 31/02* | (2006.01) | |
| *A61L 31/08* | (2006.01) | |
| *A61L 31/10* | (2006.01) | |
| *A61L 31/14* | (2006.01) | |

(52) U.S. Cl.
CPC .............. *A61L 31/022* (2013.01); *A61L 31/08* (2013.01); *A61L 31/10* (2013.01); *A61L 31/148* (2013.01)

(58) Field of Classification Search
CPC .... A61L 31/10; A61L 31/16; A61L 2300/102; A61L 2300/106; A61L 2300/404; A61L 2400/12; A61L 29/16; A61L 31/08; A61L 12/08; A61L 2400/18; A61L 2420/06; A61L 2430/00

USPC ................................................ 623/1.11–1.54
See application file for complete search history.

(56) References Cited

U.S. PATENT DOCUMENTS

| | | | |
|---|---|---|---|
| 5,925,069 A * | 7/1999 | Graves et al. ................... 607/36 |
| 2003/0004564 A1* | 1/2003 | Elkins et al. ................. 623/1.15 |
| 2005/0107870 A1* | 5/2005 | Wang et al. .................. 623/1.44 |
| 2005/0261760 A1* | 11/2005 | Weber ........................... 623/1.38 |
| 2007/0224244 A1* | 9/2007 | Weber .................... A61L 27/047 424/426 |
| 2010/0047313 A1* | 2/2010 | Priebe et al. ................. 424/423 |
| 2010/0076544 A1* | 3/2010 | Hoffmann et al. .......... 623/1.15 |

FOREIGN PATENT DOCUMENTS

| | | |
|---|---|---|
| DE | 1 036 941 | 7/2005 |
| WO | WO 1996/10454 | 4/1996 |
| WO | WO 2008/074227 | 6/2008 |
| WO | WO 2008/077248 | 7/2008 |
| WO | WO 2008/092435 | 8/2008 |

OTHER PUBLICATIONS

Das et al., Proof for a nonproteinaceous calcium-selective channel in *Escherichai coli* by total synthesis from (R)-3-hydroxybutanoic acid and inorganic polyphosphate, (Proc. Natl. Acad. Sci. USA, Aug. 1997, vol. 94, 9075-9079).*

(Continued)

*Primary Examiner* — Ann Schillinger
(74) *Attorney, Agent, or Firm* — Greer, Burns & Crain, Ltd.; Steven P. Fallon

(57) ABSTRACT

An implant includes a biocorrodible metallic material having a coating. The coating contains at least one layer in which ionic channels are embedded.

22 Claims, 1 Drawing Sheet

(56) References Cited

OTHER PUBLICATIONS

Li et al., A Small Synthetic Molecule forms Chloride Channels to Mediate Chloride Transport across Cell Membranes, (J. Am. Chem. Soc., May 16, 2007, vol. 129, 7264-7265).*
Gorteau et al. Rigid Oligonaphthalenediimide Rods as Transmembrane Anion-p Slides, (J. Am. Chem. Soc., Oct. 27, 2006, vol. 128, 14788-14789) r.*
Gorteau et al. Rigid Oligonaphthalenediimide Rods as Transmembrane Anion-p Slides, (*J. Am. Chem. Soc.*, Oct. 27, 2006, vol. 128, 14788-14789).
Gorteau, Virginie, et al., "Rigid-rod anion-π slides for multiion hopping across lipid bilayers", *Org. Biomol. Chem.*, 2007, 5, pp. 3000-3012.

* cited by examiner

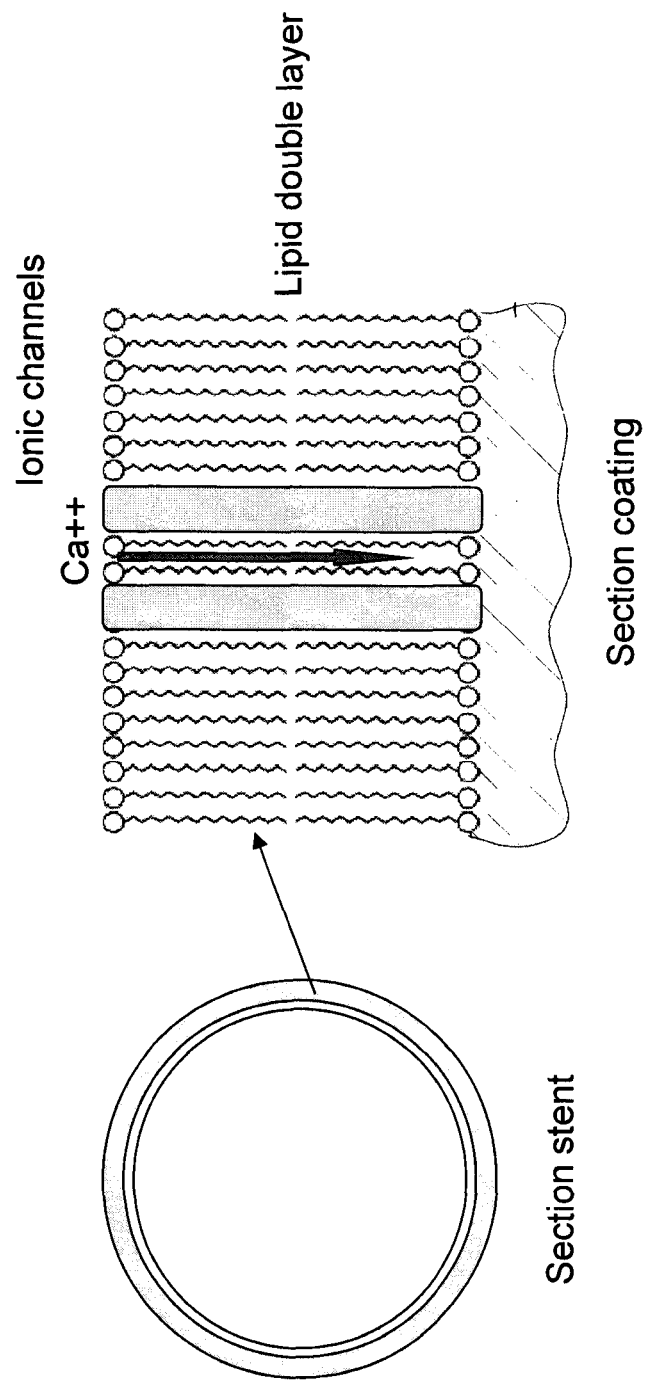

BIOCORRODIBLE IMPLANTS HAVING A FUNCTIONALIZED COATING

CROSS REFERENCE

The present application claims priority on U.S. Provisional Application No. 61/288,348, filed Dec. 21, 2009, which application is incorporated by reference herein.

TECHNICAL FIELD

One embodiment of the invention relates to a medical implant having a coating.

BACKGROUND

Implants are used in modern medical technology in a variety of embodiments. For example, they are used to support blood vessels, hollow organs and duct systems (endovascular implants, e.g., stents), for securing and temporary fixation of tissue implants and tissue transplants, but also for orthopedic purposes, e.g., as nails, plates or screws. Frequently only a temporary supporting and/or holding function is necessary or desired until conclusion of the healing process or stabilization of the tissue. To avoid complications resulting from implants remaining permanently in the body, the implants must then be removed by surgery or be made of a material that is gradually degraded in the body, i.e., is biocorrodible. The number of biocorrodible materials based on polymers or alloys has grown steadily. Biocorrodible metal alloys of the elements magnesium, iron and tungsten are known. A stent is a form of an implant that is often used.

Implantation of stents has become established as one of the most effective therapeutic measures for treatment of vascular diseases. The purpose of stents is to assume a supporting function in the hollow organs of a patient. Stents of a traditional design therefore have a filigree supporting structure of metallic struts, which are initially present in a compressed form for insertion into the body and are widened at the site of application. One of the main fields of application of such stents is for permanent or temporary dilatation of vasoconstrictions, in particular constrictions (stenoses) of the coronary vessels, and maintaining their patency. In addition, aneurysm stents, for example, which are used to support damaged vascular walls, are also known.

Stents have a circumferential wall of a sufficient load-bearing capacity to keep the stenosed vessel open to the desired extent and have a tubular base body through which the blood flow passes unimpeded. The circumferential wall is usually formed by a mesh-like supporting structure, which allows the stent to be inserted in a compressed state with a small outside diameter as far as the stenosis in the respective vessel to be treated and to widen it there with the help of a balloon catheter, for example, so that the vessel has the desired enlarged inside diameter. A cardiologist must monitor the positioning and expansion of the stent during the procedure and the subsequent position of the stent in the tissue after the end of the procedure. This may be accomplished by imaging methods, e.g., by X-ray examinations.

The stent has a base body of an implant material. An implant material is a nonviable material, which is used for an application in medicine and which interacts with biological systems. The basic prerequisites for use of a material as an implant material, which is in contact with the biological environment when used as intended, is its biocompatibility. The term biocompatibility is understood to refer to the ability of a material to induce an appropriate tissue response in a specific application. This includes adaptation of the chemical, physical, biological and morphological surface properties of an implant to the recipient tissue with the goal of a clinically desired interaction. The biocompatibility of the implant material also depends on the chronological course of the reaction of the biosystem into which the implant is implanted. Thus, relatively short-term irritation and inflammation may occur, which may lead to tissue changes. Biological systems thus react in different ways, depending on the properties of the implant material. Implant materials can be subdivided into bioactive, bioinert and degradable/resorbable materials according to the response of the biosystem.

Implant materials for stents include polymers, metallic materials and ceramic materials (e.g., as a coating). In the area of biocorrodible stents, the use of magnesium or pure iron and biocorrodible base alloys of the elements magnesium, iron, zinc, molybdenum and tungsten is proposed.

In particular when using biocorrodible materials for implants, e.g., stents, suitable control of the corrosion rate of the respective implant after implantation in the body is a field with a need for further optimization. The corrosion rate is to be implemented so that the implant can also fulfill the proper task or function in the body over the desired period of time. In the case of a stent, the integrity of the stent should be ensured for a period of time which is sufficient to fulfill the respective medical purpose. On the other hand, the advantage of biocorrodible stents is that these stents need not remain in the body for an unlimited period of time or even be removed surgically, but instead are degraded and disposed of by the body after a while. The integrity of a biocorrodible stent should be ensured over a period of time, which is as long as necessary but as short as possible.

In particular, stents having a base body consisting entirely or partially of iron or an iron alloy tend to corrode too slowly. Stents having a base body consisting entirely or partially of magnesium or a magnesium alloy often have a corrosion rate in the body that is too high.

SUMMARY

A feature of one example of the present invention is to reduce or prevent the disadvantages of the prior art.

This feature is achieved in some example embodiments by providing an implant, said implant consisting entirely or partially of a biocorrodible metallic material and having a coating, characterized in that the coating contains at least one layer in which ionic channels are embedded. In particular the ionic channels in at least some embodiments may be embedded in a lipid double layer.

The inventive implant is preferably a stent, although other implants are contemplated.

BRIEF DESCRIPTION OF THE DRAWINGS

FIG. 1 is a sectional view of an example stent according to one embodiment of the present invention, including an enlarged view of the stent coating.

DETAILED DESCRIPTION

At least some embodiments of the present invention are based on the discovery that the corrosion rate of an implant can be influenced and controlled by influencing and controlling the concentration of ions at the site of the corrosion. This can be achieved according to some invention embodiments by providing the implant with a coating comprising ionic channels. It has been discovered that through the choice of suitable ionic channels, the concentration of certain ions at the site of the corrosion can be influenced as needed. Through the choice of certain ionic channels, the concentration of selected ions at the site of the corrosion can be increased and the corrosion rate thereby influenced. For example, biocorrodible implants comprising or consisting of a magnesium alloy can have post-implantation corrosion rates that may lead to a premature loss of implant integrity. If such implants are provided through invention embodiments with a coating comprising ionic channels, which are specifically permeable for Ca cations, the corrosion rate of the implant can be retarded. On the other hand, implants comprising or consisting of pure iron or an iron alloy may have corrosion rates that lead to degradation of the implant, which proceeds too slowly. For example, if such implants are provided through invention embodiments with a coating containing ionic channels specific for Cl anions, then the corrosion rate of such implants can be increased in this way.

One example inventive implant consists entirely or partially of a biocorrodible metallic material. This biocorrodible material is preferably a magnesium alloy. This biocorrodible material may also be iron or an iron alloy. The biocorrodible implant preferably contains a metallic base body. In particular the metallic base body may consist of magnesium, a biocorrodible magnesium alloy, pure iron, a biocorrodible iron alloy, a biocorrodible tungsten alloy, a biocorrodible zinc alloy or a biocorrodible molybdenum alloy.

Biocorrodible in the sense of the present invention refers to alloys and elements in which degradation/rearrangement takes place in a physiological environment, so that the part of the implant consisting of the material is no longer present in all, either entirely or at least predominantly.

A magnesium alloy, iron alloy, zinc alloy, molybdenum alloy or tungsten alloy here is understood to be a metallic structure whose main component is magnesium, iron, zinc, molybdenum or tungsten. The main component is the alloy component whose proportion by weight in the alloy is greatest. The proportion of the main component is preferably more than 50 wt %, in particular more than 70 wt %. The composition of the alloy is selected so that it is biocorrodible. The test medium used for testing the corrosion behavior of an alloy in question is artificial plasma, such as that stipulated according to EN ISO 10993-15:2000 for biocorrosion tests (composition NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L). A sample of the alloy to be tested is stored in a sealed sample container with a defined quantity of the test medium at 37° C. At intervals of a few hours up to several months (depending on the corrosion behavior to be expected), the samples are removed and examined for traces of corrosion in a known way. The artificial plasma according to EN ISO 10993-15:2000 corresponds to a medium resembling blood and thus constitutes one possibility of reproducibly simulating a physiological environment in the sense of the invention.

According to the invention, the implant has a coating. A coating in the sense of the invention is an application of the components of the coating to the base body of the implant in at least some sections. The entire surface of the base body of the implant is covered by the coating in at least some invention embodiments, while in others less than the entire surface is covered. The layer thickness may be in the range of 1 nm to 10 µm, may be 2 nm to 50 nm, or may be in other ranges with some less than 1 nm and others great than 50 nm. The coating may be applied directly to the implant surface. The processing may be performed according to standard methods for coating. The coating is preferably applied by immersion. Single-layer or multilayer systems (e.g., so-called base coat, drug coat or topcoat layers) may be created. The coating may be applied directly to the base body of the implant or other layers may also be provided between the base body and the inventive coating.

The coating of some inventive implant embodiments comprises or consists of at least one layer having ionic channels, optionally embedded in a lipid double layer and in some but not all embodiments covering the entire surface of the implant.

An ionic channel is understood here to be a structure, which forms a lumen or a pore through which ions can move or be moved. For example, if an ionic channel is embedded in a lipid double layer, then the ionic channel is aligned directionally in the lipid double layer, so that passage of ions from one side of the lipid double layer to the other side of the lipid double layer is made possible through the lumen or the pore of the ionic channel. An ionic channel here usually has an amphiphilic character, such that nonpolar radicals are predominant on the outside facing the lipid double layer and polar or charged radicals are present on the side facing the lumen. The ionic transport through an ionic channel preferably takes place along an existing electrochemical gradient, the concentration and potential gradient. The transport from one side of the lipid double layer to the other side is thus passive without requiring any additional input of energy.

An ionic channel usually consists of multiple molecules, such that an ionic channel may have or comprise multiple different subunits. In a simple exemplary structure, an ionic channel has a plurality of molecules of a first subunit arranged "like a barrel" so that the ionic channel is differentiated from the lipid double layer in which it is embedded and forms a lumen or a pore in the middle. One or more molecules of a second subunit may be arranged on the inside of the lumen and may be of a type such that transport of preferably a certain type of ions through the ionic channel is made possible. Those skilled in the art will be aware of suitable ionic channels, and overly extensive detail regarding the same is not necessary and omitted herein for sake of brevity. Ionic channels comprising biocompatible compounds and/or substances are suitable for use in many embodiments, although other types are used in other embodiments.

For example, ionic channels comprising or consisting entirely or partially of polypeptide structures may be used in some invention embodiments. Polypeptide structures are understood to be structures comprising at least two proteinogenic amino acids linked together by a peptide bond, Peptide structures comprise dipeptides, oligopeptides, polypeptides and proteins as well as protein fragments.

However, ionic channels that are peptide-free, i.e., consist of organic molecules or arrangements of organic molecules (also containing inorganic molecules, if necessary), which do not have at least two proteinogenic amino acids joined together by a peptide bond, may also be used.

An interesting property of certain ionic channels that is exploited in some invention embodiments is that they may be selective for the transport of selected ions. Some or all ionic channels in the coating of the inventive implant may be selective ionic channels. The term "selectivity" is understood to mean that ions having certain properties or ions of a certain type are transported preferentially, whereas ions that do not have these properties or ions of a different type are not transported at all or not as well. This selectivity may be achieved, for example, by the fact that the lumen of the ionic channel is of a type such that only ions of a certain size can pass through it, whereas ions exceeding this size are prevented from passing. However, selectivity of an ionic channel can also be achieved through specific interactions between the ions to be transported and components of the ionic channel.

For example, ionic channels that are selective for cations, in particular selective for Ca, K and/or Na cations, especially preferably for Ca cations with the oxidation state +2, may be used in some embodiments. In particular, some or all of the ionic channels of an inventive implant may be selective for cations, preferably for Ca cations. Implants consisting entirely or partially of a magnesium alloy especially preferably have a coating, in which some or all of the ionic channels are selective for Ca cations, preferably $Ca^{2+}$ cations.

One example of an ionic channel that is selective for the transport of cations, in particular Ca cations, and is useful for practice of some invention embodiments is described by Das et al. (*Proc. Natl. Acad. Sci. USA*, 1997, vol. 94, 9075-9079). These are ionic channels, which include the amphiphilic homopolymer poly(3-hydroxybutyrate) (PHB). A PHB polymer preferably comprises 115 to 150 monomer radicals. Ionic channels comprising or consisting of the two structurally different polymers PHB and calcium polyphosphate (Ca(polyP)) are especially preferred for use here. PHB homopolymers having 115 to 150 monomer radicals and Ca(polyP) as the Ca salt of polyP anions having 50 to 80 phosphate radicals are preferred in the ionic channels comprising PHB and Ca(polyP).

However, ionic channels that are selective for anions, in particular selective for Cl, nitrate and/or malate anions, especially preferably for Cl anions having an oxidation state of −1, may also be used. In particular some or all ionic channels of an inventive implant may be selective for anions, preferably for Cl anions. Implants consisting entirely or partially of pure iron or an iron alloy especially preferably have a coating in which some or all of the ionic channels are selective for Cl anions, preferably Cl⁻ ions.

An example of an anionic channel that is selective for the transport of Cl anions and useful in some invention embodiments is described by Li et al (*J. Am. Chem. Soc.*, 2007, vol. 129, 7264-7265). This discloses the use of an ionic channel comprising or consisting of a plurality of molecules of compound 1, where compound 1 is:

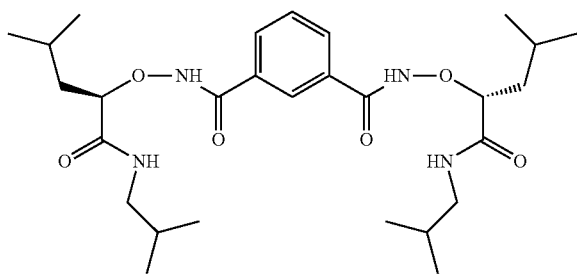

1

In at least some embodiments of the inventive implant, some or all ionic channels may comprise compound 1 or consist of compound 1 and/or a plurality thereof.

Another example of an ionic channel that is selective for transport of Cl anions is described by Gorteau et al. (*J. Am. Chem. Soc.*, 2006, vol. 128, 14788-14789). The ionic channels are characterized in that they comprise rod-shaped oligo-(p-phenylene)-N,N-naphthalene-diimide (O-NDI) or consist of a plurality of rod-shaped O-NDI molecules, where the term "oligo" stands for a number of monomers from 2 to 20. The term "O-NDI" explicitly also includes those rod-shaped oligo-(p-phenylene)-N,N-naphthalenediimides, in which one or both terminal amines are substituted or modified. For example, a hydrogen of one or both terminal amines of an O-NDI molecule may be substituted by a protective group, e.g., by a tert-butyloxycarbonyl (BOC) group. However, one or both terminal amines may also be present in the form of ammonium, preferably an ammonium salt, in particular an ammonium salt with trifluoroacetic acid (TFA). In the inventive implant, some or all of the ionic channels may comprise an oligo-(p-phenylene)-N,N-naphthalenediimide (O-NDI) molecule or may consist of one or a plurality of O-NDI molecules.

The coating of some embodiments of an inventive implant may have exclusively ionic channels of a single type or may have a mixture of different ionic channels, preferably of a different selectivity.

In one embodiment of the inventive implant, the ionic channels are embedded in a lipid double layer. A lipid double layer is a structure formed by a plurality of amphiphilic lipids in the presence of a polar solvent, such that a membrane develops, in which the hydrophobic part of the amphiphilic lipids forms the core of the membrane and the hydrophilic part forms the outsides bordering the membrane. An important property of lipid double layers is that they are almost impermeable for polar molecules or macromolecules but at the same time are very flexible and mechanically difficult to destroy. The lipid double layer preferably comprises or consists of amphiphilic lipids. These are especially preferably biocompatible amphiphilic lipids. The lipid double layer most especially preferably comprises or consists of phospholipids, phosphoglycerides, sphingolipids, phosphatidylethanolamines, phosphatidylserines, phosphatidylcholines, sphingomyelins and/or plasmalogens as well as mixtures thereof.

Because of their amphiphilic character, the ionic channels may be independently organized and aligned in the lipid double layer, if necessary, so that the ionic channels are present in a functional orientation and allow a transport of ions between the two sides of the lipid double layer.

Those skilled in the art are aware of many suitable methods of applying a coating comprising a layer having ionic channels embedded in a lipid double layer. Preferred methods include dipping, coating in a Langmuir-Blodgett method, spraying, "self-assembly" methods, rotational coating and/or "drop casting" methods. Other methods will also find use in practice of various invention embodiments.

The inventive coating may contain additional substances, with examples including pharmaceutical active ingredients, X-ray markers, magnetic resonance markers, and others.

Various aspects of invention embodiments are explained in greater detail below on the basis of exemplary embodiments. It will be appreciated that many additional examples of embodiments are possible, and the below examples are not intended to limit the scope of the invention as claimed in any way.

EXAMPLE 1

A solution of the complex of poly(3-hydroxybutyrate) (PHB) and inorganic polyphosphate (polyP) in chloroform was prepared by mixing a solution of PHB (1 µg/mL) in chloroform with Ca(polyP) which had been prepared previously from sodium phosphate and CaCl.

To the PHB-polyp polymer solution was added a solution of dimyristoyl-phosphatidylcholine (DMPC) in chloroform with DMPC in a concentration of 0.9 mg/ml. Drops (20 μL) of the solution thus prepared are distributed randomly over an aqueous subphase in a Langmuir-Blodgett device. The resulting floating film was compressed linearly by two mobile plates at a rate of 5 mN m$^{-1}$ min$^{-1}$. The resulting film was transferred to a stent by stripping.

EXAMPLE 2

A stent was provided with a coating having ionic channels by immersing it for three minutes in the PHB-polyP polymer solution from Example 1. The stent coated in this way was then air-dried.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implant comprising a biocorrodible metallic material and having a coating applied to and covering at least some sections of the metallic material, the coating comprising lumens or pores defining ionic channels that selectively transport ions to the metallic material through the coating, wherein the lumens or pores selectively transport only one of anions or cations to respectively increase or retard a corrosion rate of the metallic material.

2. The implant according to claim 1, characterized in that the ionic channels are embedded in a lipid double layer.

3. The implant according to claim 2, characterized in that the lipid double layer comprises one or more of amphiphilic lipids, biocompatible amphiphilic lipids, phospholipids, phosphoglycerides, sphingolipids, phosphatidylethanolamines, phosphatidylserines, phosphatidylcholines, sphingomyelins and plasmalogens, as well as mixtures thereof.

4. The implant according to claim 1, characterized in that the biocorrodible metallic material is a magnesium alloy and wherein said embedded ionic channels transport ions between an external environment and the metallic material.

5. The implant according to claim 1, characterized in that the biocorrodible metallic material is one of iron or an iron alloy and the lumens or pores selectively transport anions that increase the corrosion rate of the iron or iron alloy.

6. The implant according to claim 1, characterized in that the at least one layer has exclusively ionic channels of a single type.

7. The implant according to claim 1, characterized in that at least some of the ionic channels have polypeptide structures.

8. The implant according to claim 1, characterized in that at least some of the ionic channels are peptide-free.

9. The implant according to claim 1, characterized in that at least some of the ionic channels are selective.

10. The implant according to claim 1, characterized in that at least some of the ionic channels are selective for cations.

11. The implant according to claim 10 wherein the at least some of the ionic channels are selective for Ca cations to retard the corrosion rate of the metallic material.

12. The implant according to claim 1, characterized in that some or all of the ionic channels are selective for anions.

13. The implant according to claim 12 wherein the at least some of the ionic channels are selective for Cl anions to enhance the corrosion rate of the metallic material.

14. The implant according to claim 1, characterized in that at least some of the ionic channels comprise poly(3-hydroxybutyrate)(PHB).

15. The implant according to claim 1 wherein at least some of the ionic channels comprise PHB and calcium polyphosphate (Ca(polyP)).

16. The implant according to claim 1 wherein at least some of the ionic channels comprise PHB polymers with 115 to 150 monomer radicals and Ca(polyP) with 50 to 80 phosphate radicals.

17. The implant according to claim 1, characterized in that at least some of the ionic channels comprise a plurality of compound 1, where compound 1 is:

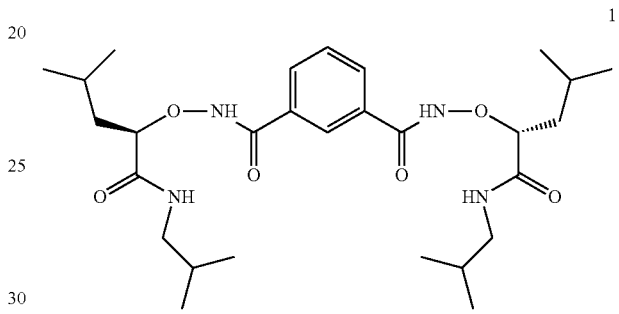

18. The implant according to claim 1, characterized in that at least some of the ionic channels comprise an oligo-(p-phenylene)-N,N-naphthalenediimide (O-NDI) molecule.

19. The implant according to claim 1, wherein the embedded ionic channels are aligned in a radial direction relative to the implant and have an electrochemical gradient that transports ions.

20. The medical implant according to claim 1, consisting of the metallic material and the coating comprising lumens or pores defining ionic channels.

21. A medical implant comprising:
a magnesium alloy base body; and,
a coating applied to and covering substantially all of an exterior surface of the base body and having ionic channels imparting permeability to the coating for selective transport of ions from external of the coating to the base body through the coating, said ionic channels being selective for Cl anions and comprising at least one of (O-NDI) and the compound 1, where compound 1 is:

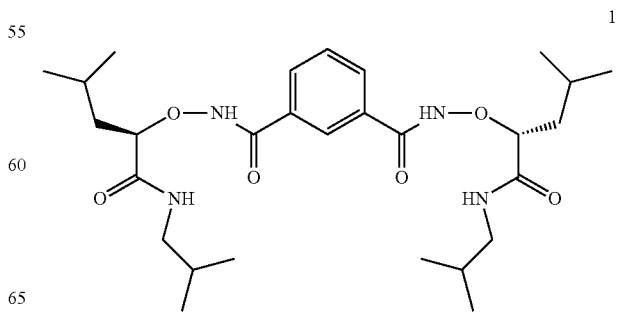

22. The medical implant according to claim 21, the embedded ionic channels having an electrochemical gradient that transports ions.

\* \* \* \* \*